United States Patent
Wang et al.

(10) Patent No.: US 11,401,247 B2
(45) Date of Patent: Aug. 2, 2022

(54) THIAZOLE-5-CARBOXYLIC ACID DERIVATIVE AND PREPARATION METHOD AND USE THEREOF

(71) Applicant: XIANGBEI WELMAN PHARMACEUTICAL CO., LTD, Hunan (CN)

(72) Inventors: Haiyong Wang, Hunan (CN); Mingjie Sun, Hunan (CN)

(73) Assignee: XIANGBEI WELMAN PHARMACEUTICAL CO., LTD, Hunan (CN)

( * ) Notice: Subject to any disclaimer, the term of this patent is extended or adjusted under 35 U.S.C. 154(b) by 70 days.

(21) Appl. No.: 16/963,083

(22) PCT Filed: Jan. 18, 2019

(86) PCT No.: PCT/CN2019/072273
§ 371 (c)(1),
(2) Date: Jul. 17, 2020

(87) PCT Pub. No.: WO2019/144842
PCT Pub. Date: Aug. 1, 2019

(65) Prior Publication Data
US 2021/0024474 A1    Jan. 28, 2021

(30) Foreign Application Priority Data
Jan. 23, 2018  (CN) .......................... 201810064046.8

(51) Int. Cl.
| C07D 277/56 | (2006.01) |
| C07D 417/06 | (2006.01) |
| C07H 15/26  | (2006.01) |
| A61P 19/06  | (2006.01) |

(52) U.S. Cl.
CPC ............ C07D 277/56 (2013.01); A61P 19/06 (2018.01); C07D 417/06 (2013.01); C07H 15/26 (2013.01)

(58) Field of Classification Search
None
See application file for complete search history.

(56) References Cited

U.S. PATENT DOCUMENTS 5,614,520 A    3/1997   Kondo et al.

FOREIGN PATENT DOCUMENTS

| CN | 102643249 A | 8/2012 | |
| CN | 103880775 A | 6/2014 | |
| CN | 105218479 A | 1/2016 | |
| EP | 2404903 A1 | 1/2012 | |
| WO | 1992009279 A1 | 6/1992 | |
| WO | 2011073617 A1 | 6/2011 | |
| WO | WO-2015196323 A1 * | 12/2015 | ........... A61K 31/427 |

OTHER PUBLICATIONS

Kitamura et al., Crystal Growth and Design—vol. 7, No. 9, 2007, pp. 1575-1579. (Year: 2007).*
Grabowski et al., Journal of Clinical Pharmacology, 2011, vol. 51(2), pp. 189-201. (Year: 2011).*
English Translation of PCT/CN2019/072273 dated Apr. 25, 2019.
Sekhar, Kuruva Chandra et al., "Augmenting the Xanthine Oxidase Inhibitory Activity of Febuxostat by its Structural Modification", Letters in Drug Design & Discovery, vol. 2, No. 11, Dec. 31, 2014.
English Abstract of CN-105218479, Publication Date: Jan. 6, 2016.
English Abstract of CN-102643249, Publication Date: Aug. 22, 2012.
English Abstract of CN-103880775, Publication Date: Jun. 25, 2014.
Sekhar: Augmenting the Xanthine Oxidase Inhibitory Activity , Letters in Drug Design & Discovery, 2014, II, 207-210.
Hauenschild ; Characterizing Active Pharmaceutical Ingredient Binding to Human Serum Albumin by Spin-Labeling and EPR Spectroscopy; Chem. Eur. J. 2016, 22,(36), 12825-12838.
Kilaru et al.: Design, synthesis, in silico and in vitro studies of novel 4-methylthiazole-5-carboxylic acid derivatives as potent anti-cancer agents; Bioorg. Med. Chem. Lett. 24 (2014) 4580-4585.
English Translation of Notice of Reasons for Refusal in corresponding Japanese Patent Application No. 2020-538899 (pp. 1-3) dated Aug. 2021.
Hu: Febuxostat in the management of hyperuricemia and chronic gout: a review; Therapeutics and Clinical Risk Management 2008:4(6) 1209-1220.
M. Mukoyoshi: In vitro drug-drug interaction studies with febuxostat, a novel non-purine selective inhibitor of xanthine oxidase: plasma protein binding, identification of metabolic enzymes and cytochrome P450 inhibition; . Xenobiotica May 2008; 38(5): 496-510.

(Continued)

Primary Examiner — Traviss C McIntosh, III
(74) Attorney, Agent, or Firm — Millen, White, Zelano & Branigan, PC; Ryan Pool

(57) ABSTRACT

The present disclosure relates to a thiazole-5-carboxylic acid derivative represented by Formula (I), a stereoisomer and/or pharmaceutically acceptable salt thereof. The compound of Formula (I), the stereoisomer and/or pharmaceutically acceptable salt thereof of the present disclosure can be used to prepare a medicament for preventing or treating hyperuricemia and/or gout, and can be prepared into dosage forms for various administration routes. The compounds provided in the present disclosure have good tolerance, safety and excellent uric acid-lowering activity.

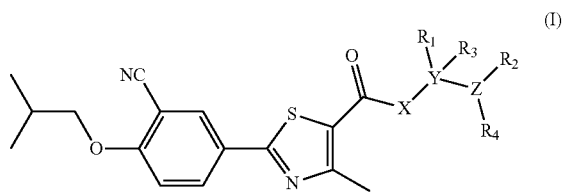

9 Claims, No Drawings

(56) References Cited

OTHER PUBLICATIONS

Notice of Reasons for Refusal in corresponding Japanese Patent Application No. 2020-538899 (pp. 1-3) dated Aug. 2021.
Partial Supplementary European Search Report in corresponding EP19743215 (pp. 1-6) dated Jul. 7, 2021.
Supplementary European Search Report dated Oct. 22, 2021 in corresponding EP19743215 (pp. 1-14).

* cited by examiner

THIAZOLE-5-CARBOXYLIC ACID DERIVATIVE AND PREPARATION METHOD AND USE THEREOF

CROSS-REFERENCE TO RELATED APPLICATIONS

This application is based on and claims the benefit of priority from Chinese Patent Application No. 201810064046.8, filed on Jan. 23, 2018, the entirety of which is incorporated by reference herein.

TECHNICAL FIELD

The present disclosure relates to the field of medicine, in particular to thiazole-5-carboxylic acid derivatives, as well as the preparation method and use thereof.

BACKGROUND

Gout is a group of syndromes caused by abnormal purine metabolism in a human body, and hyperuricemia is one stage during the development of this disease. According to developed condition characteristics, primary gout may progress along four stages: asymptomatic hyperuricemia stage, acute attack stage, asymptomatic intermittent stage and chronic stage. There are main clinical manifestations as follows: (1) Asymptomatic hyperuricemia. Asymptomatic hyperuricemia has a highly insidious onset, with intermittent occurrence at early stage and progressing gradually to a persistent condition. (2) Acute gouty arthritis. It is the most characteristic and common condition of gout, and has an abrupt onset. Involved joints can have obvious redness and heat pain in a few hours. Since acute gouty arthritis often attacks at night, people would wake up due to severe joint pain, affected joints cannot be touched due to pain and even cannot be covered with bed-sheet, with limited mobility. (3) Intermittent stage of gout. The intermittent stage of gout refers to an interval between two episodes of acute gouty arthritis, and ranges from a few weeks to a few decades. Hyperuricemia may still exist, and the level of blood uric acid may be unstable depending on diet and treatment. (4) Chronic tophaceous gout. If hyperuricemia is not repaired for a long term, urate crystals would be widely deposited in articular cartilage, synovium, ligament, subcutaneous tissues and kidney, and gradually form urate stones which will affect the physiological functions of the deposited tissues when the condition becomes serious. (5) Subcutaneous tophus nodules. Subcutaneous tophus nodules are formed from urate crystals deposited under skin, and are more likely to occur around helixes and joints. (6) Chronic gouty arthritis. Repeated and multiple attacks of acute arthritis caused the fibrosis of joint tissues and the formation of tophus in articular cartilage, synovium and ligaments, resulting in gradual destruction and deformation of affected joints and in loss of exercise capacity. (7) Chronic gouty nephropathy, and kidney calculi or urate crystals. There are two types of urate deposition in kidney, including urate deposition outside renal tubules caused by insufficient excretion and discharge of uric acid, and urate deposition within renal tubules caused by uric acid which is remained in the renal tubules due to excessive concentration and being not discharged in time. Chronic uric acid nephropathy may develop on the basis of these two types of uric acid deposition in kidney.

In clinical practice, secondary gout manifests with clinical features of a secondary disease before the occurrence of hyperuricemia. Secondary gout mostly has acute attacks, but the cases caused by congenital renal tubular dysfunction and chronic renal failure have slow onset. Acute renal failure caused by hyperuricemia and deposition of a large amount of urate in renal tubules is common, in which the uric acid level can be >1 mmol/L in blood and obviously increased in urine, a large number of urate crystals can be seen in urinary sediment, and hematuria can be occasionally observed by microscopy or naked eye. Patients may experience symptoms such as asurinary pain, low back pain, nausea, emesis, oliguria or anuria.

The treatment of gout includes two aspects, one is relieving inflammatory and pain, the other is reducing blood uric acid. The former is to cure the symptoms; the latter is to cure the disease. It would apply symptomatic treatment in acute condition, and finally achieve the goal of curing both the symptoms and disease. Correspondingly, there are two categories of drugs. The first category comprises inflammatory- and pain-relieving drugs, mainly includes: (1) Colchicine. Colchicine can prevent cell mitosis, inhibit the chemotaxis of inflammatory cells, reduce the release of inflammatory factors, and has a unique effect of relieving inflammatory and swelling for acute attack of gouty arthritis. (2) Nonsteroidal antiinflammatory drugs. There are many kinds of nonsteroidal antiinflammatory drugs, which mainly reduce local soft tissue redness, heat pain and systemic reaction during the attack of acute gouty arthritis, through inhibiting inflammatory response of tissues to uric acid deposition, without affecting serum uric acid level. (3) Adrenal glucocorticoids. For patients having particularly severe symptoms of acute gouty arthritis or having colchicine intolerance, a small or medium dose of prednisone and dexamethasone can be used to reduce the inflammatory response of tissues. The second category comprises uric acid-lowering drugs. The production of uric acid in a body is related to purine metabolism. In the final step of purine metabolism, hypoxanthine produces xanthine under the action of xanthine oxidoreductase (XOR), and further produces uric acid. It can effectively reduce the production of uric acid by inhibiting the activity of this enzyme. The uric acid-lowering drugs mainly exert the effect of lowering uric acid by inhibiting the production of uric acid in a body and promoting the discharge of uric acid from blood. Main drugs of this category are as follows: (1) Probenecid. This drug can inhibit the reabsorption of urate by renal tubules, thereby increasing the discharge of uric acid from kidney. It is applicable for gout patients having a high blood uric acid level and having a urinary uric acid discharge rate <3.6 mmol/d (<600 mg/d). (2) Benzbromarone (exurate). This drug promotes the excretion of uric acid by inhibiting the reabsorption of uric acid by proximal renal tubules, without inhibiting the metabolism of purine nucleotides. It is mainly discharged through a gastrointestinal tract (intrahepatic metabolism, bile discharge), and is suitable for gout patients with urinary uric acid discharge rate <3.6 mmol/d, and for gout patients with mildly elevated inosine and early renal insufficiency. (3) Allopurinol. This drug is a xanthine oxidase inhibitor, and inhibits the conversion of hypoxanthine to xanthine and then to uric acid, thereby reducing the synthesis of uric acid. It is suitable for primary or secondary gout patients who produce excessive uric acid. (4) Febuxostat. Febuxostat has a significant inhibitory effect on both oxidized and reduced XOR, and thus has more powerful and long-lasting uric acid-lowering effect. Therefore, it can be used to treat chronic gouty hyperuricemia.

However, the existing drugs for treating gout or lowering uric acid still have strong side effects and are poorly tolerated. For example, colchicine and nonsteroidal antiinflammatory drugs have obviously gastrointestinal adverse reaction. Long-term use of adrenal glucocorticoid drugs can lead to metabolism and hormone disorders. Probenecid can cause gastrointestinal ulcers and kidney calculi. Benzbromalone can cause severe liver damage. Allopurinol can cause severe drug rashes. Febuxostat can cause abnormal liver function and renal tubular nephritis, increase cardiovascular adverse reactions, and the like. Therefore, it has very important clinical significance to develop drugs with better safety and excellent therapeutic effects for treating gout or reducing uric acid.

SUMMARY

The objective of the present disclosure is to provide a class of compounds, i.e. thiazole-5-carboxylic acid derivatives, that have better tolerance and safety, and also have excellent therapeutic effects for treating gout or reducing uric acid.

In particular, the thiazole-5-carboxylic acid derivative of the present disclosure refers to a compound represented by Formula (I), a stereoisomer and/or pharmaceutically acceptable salt thereof:

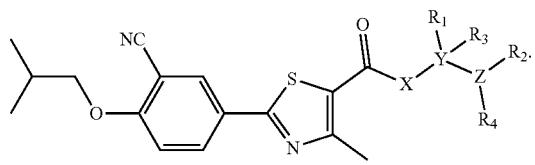
(I)

In Formula (I), X is selected from oxygen or nitrogen; Y and Z are both carbon.

Wherein, X selecting from oxygen means that X is

X selecting from nitrogen means X is

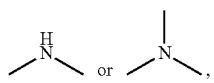

that is, X may be a secondary or tertiary amino group.

Each of $R_1$, $R_2$, $R_3$, $R_4$ is independently selected from a hydrogen atom, halogen, oxo, and substituted or unsubstituted amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl, provided that not all $R_1$, $R_2$, $R_3$ and $R_4$ are hydrogen atoms.

In Formula (I), one or more of $R_1$, $R_2$, $R_3$ and $R_4$, together with one or more atoms of X, Y and Z, may form a saturated five-membered ring, a saturated six-membered ring or a derivative structure thereof, provided that a saturated six-membered ring composed of $R_3$ or $R_4$, together with X, Y, and Z, is excluded.

Alternatively, each of one or more hydrogen atoms in the above $R_1$, $R_2$, $R_3$ and $R_4$ groups may optionally be independently further substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, alkyl, hydroxyalkyl, carboxyalkyl, aminoalkyl or alkylaminoalkyl.

The present disclosure further has preferred embodiments for each group in Formula (I). In particular:

In Formula (I), each of $R_1$, $R_2$, $R_3$ and $R_4$ is independently selected from a hydrogen atom (H—), halogen (X—), hydroxyl (HO—), oxo (O=), aldehyde (—CHO), carboxyl (—COOH), amino ($H_2N$—), alkyl ($R_n$—), halogenated alkyl (X—$R_n$—), aminoalkyl ($H_2N$—$R_n$—), alkoxy ($R_n$—O—), alkylcarbonyl

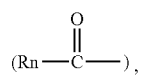

alkylcarbonyloxy

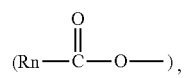

alkyloxycarbonyl

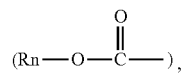

mono- or di-alkyl substituted amino ($R_n$—NH— or

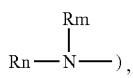

alkylaminoalkyl ($R_n$—NH—$R_m$— or

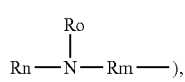

alkylaminoalkyloxycarbonyl ($R_n$—NH—$R_m$—O—CO— or

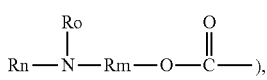

hydroxylalkyl (HO—$R_n$—), carboxylalkyl

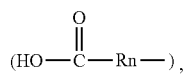

aminoalkyl ($H_2N$—$R_n$—); and not all $R_1$, $R_2$, $R_3$ and $R_4$ are hydrogen atoms.

In Formula (I), each of one or more hydrogen atoms in $R_1$, $R_2$, $R_3$ and $R_4$ groups may optionally be independently substituted by halogen (X—), hydroxyl (HO—), aldehyde (—CHO), carboxyl (—COOH), amino (H₂N—), alkyl (R$_n$—), alkoxyl (R$_n$—O—), alkylcarbonyl

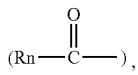, alkylcarbonyloxy

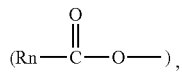, alkyloxycarbonyl

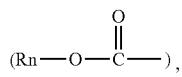, mono- or di-alkyl substituted amino (R$_n$—NH— or

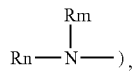), mono- or di-alkyl substituted aminoalkyl (R$_n$—NH—R$_m$— or

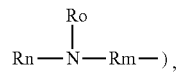), alkylaminoalkyloxycarbonyl (R$_n$—NH—R$_m$—O—CO— or

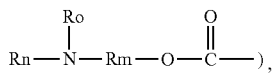), hydroxylalkyl (HO—R$_n$—), carboxylalkyl

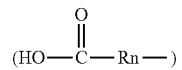

or aminoalkyl (H₂N—R$_n$—).

Further preferred in the present disclosure, each of R₁, R₂, R₃ and R₄ is independently selected from a hydrogen atom, halogen, hydroxyl, oxo, aldehyde, carboxyl, amino, alkyl, halogenated alkyl, aminoalkyl, aminoalkylamino (H₂N—R$_n$—NH— or

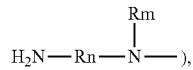), alkoxyl, alkyloxyalkyl (R$_n$—O—R$_m$—), alkyloxyalkyloxy (R$_n$—O—R$_m$—O—), alkylcarbonyl, alkylcarbonyloxy, alkyloxycarbonyl, alkylamino, alkylaminoalkyl, hydroxylalkylamino (HO—R$_n$—NH— or

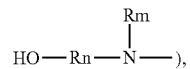), hydroxylalkylaminoalkyl (HO—R$_n$—NH—R$_m$ or

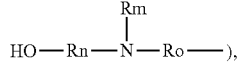), alkylaminoalkyloxycarbonyl, hydroxylalkyl, hydroxylalkyloxy (HO—R$_n$—O—), carboxylalkyl or aminoalkyl, and not all R₁, R₂, R₃ and R₄ are hydrogen atoms.

Each of the above substituents is illustrated by starting with the end group thereof. Further preferred in the present disclosure, each of the above alkyl, R$_n$, R$_m$ or R$_o$ independently represents a monovalent or divalent saturated C₁-C₄ hydrocarbyl. More particularly, these groups represent methyl, ethyl, propyl, isopropyl, butyl, isobutyl, tert-butyl, methylene, ethylene, propylene, isopropylene, butylene, isobutylene, tert-butylene.

The halogen is preferably fluorine, chlorine, bromine or iodine.

The term "oxo" in the definitions of R₁, R₂, R₃ and R₄ refers to a divalent group O═ formed by R₁ together with R₃ or by R₂ together with R₄; alternatively, R₁, R₂, R₃ and R₄, per se, can be a divalent group O═.

In a preferred embodiment of Formula (I), Y and Z, together with R₁ or R₃, and R₂ or R₄, form a saturated six-membered ring structure or a derivative structure thereof.

In a preferred embodiment of Formula (I), X, Y and Z, together with R₂ or R₄, form a saturated five-membered ring structure or a derivative structure thereof.

According to the present disclosure, the derivative structures of the saturated five- and six-membered ring structures mainly refer to the tautomer thereof, such as ring-chain tautomerism.

For example, in a preferred embodiment of the present disclosure, the saturated six-membered ring structure or derivative structure thereof is a pyranose ring or a tautomer thereof

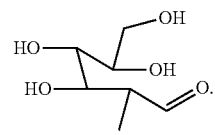

In another preferred embodiment of the present disclosure, the saturated five-membered ring structure or derivative structure thereof is preferably a pyrrole ring or a derivative structure thereof.

As the first particularly preferred embodiment of the present disclosure, in Formula (I), X is oxygen; each of R₁, R₂, R₃ and R₄ is independently selected from a hydrogen atom, halogen, hydroxyl, or alkyl; each of one or more hydrogen atoms of the alkyl group can be independently substituted by hydroxyl or halogen; provided that not all R₁, R₂, R₃ and R₄ are hydrogen atoms.

Preferably, the above alkyl group is preferably $C_1$-$C_4$ alkyl.

Preferably, at least one of the above $R_1$, $R_2$, $R_3$ and $R_4$ is a hydrogen atom.

Further preferably, the compound represented by Formula (I) is selected from one or more of the following structures:

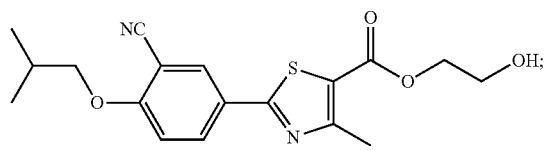

F-1A

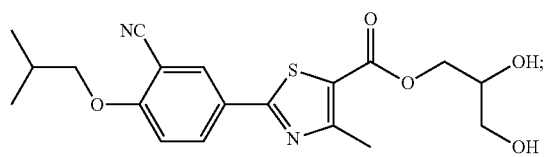

F-1B

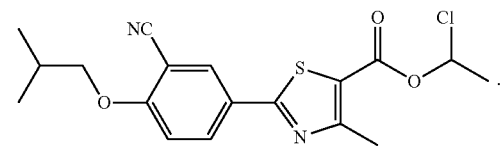

F-1C

As the second preferred embodiment of the present disclosure, in Formula (I), X is nitrogen; each of $R_1$ and $R_3$ is independently selected from a hydrogen atom, alkyl, or carboxyl; $R_2$, $R_4$ are oxo and hydroxyl, respectively, or are each independently selected from a hydrogen atom, alkyl, or carboxyl; one or more hydrogen atoms of alkyl, carboxyl, or hydroxyl can be independently substituted by carboxyl or alkyl; provided that not all $R_1$, $R_2$, $R_3$ and $R_4$ are hydrogen atoms. Wherein, when one of $R_2$ and $R_4$ is alkyl, it can, together with X, Y and Z, form a saturated five-membered ring structure or a derivative structure thereof.

Preferably, the above alkyl group is preferably $C_1$-$C_4$ alkyl.

Preferably, at least one of the above $R_1$, $R_2$, $R_3$ and $R_4$ is a hydrogen atom.

Further preferably, the compound represented by Formula (I) is selected from one or more of the following structures:

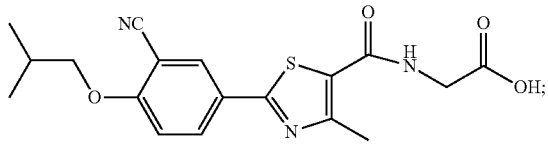

F-2A

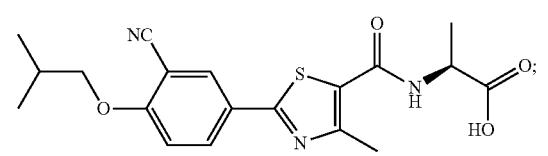

F-2B

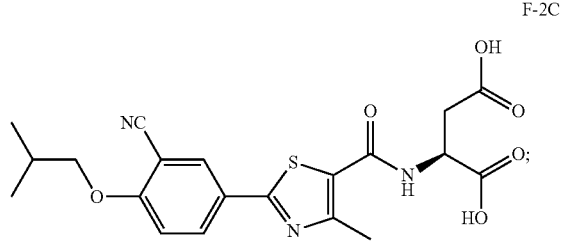

F-2C

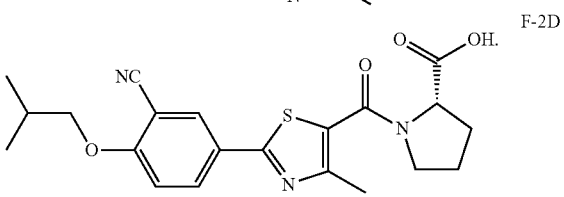

F-2D

As the third preferred embodiment of the present disclosure, in Formula (I), X is oxygen; each of $R_1$, $R_2$, $R_3$ and $R_4$ is independently selected from a hydrogen atom, aminoalkyl, alkylamino, hydroxylalkyl, amino or alkyl; one or more hydrogen atoms of the aminoalkyl, alkylamino, hydroxylalkyl, amino or alkyl can be independently substituted by alkyl, aminoalkyl, alkylamino, hydroxylalkyl, hydroxyl; provided that not all $R_1$, $R_2$, $R_3$ and $R_4$ are hydrogen atoms.

Preferably, the above alkyl group is preferably $C_1$-$C_4$ alkyl.

Preferably, at least one of the above $R_1$, $R_2$, $R_3$ and $R_4$ is a hydrogen atom.

Further preferably, the compound represented by Formula (I) is selected from one or more of the following structures:

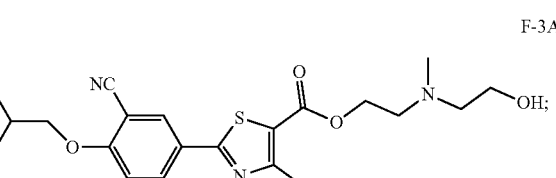

F-3A

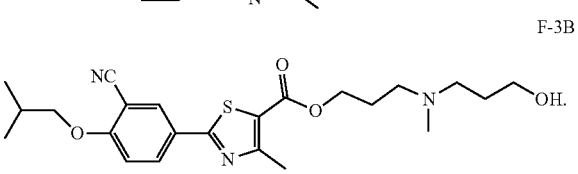

F-3B

As the fourth preferred embodiment of the present disclosure, in Formula (I), X is nitrogen; each of $R_1$ and $R_3$ is independently selected from a hydrogen atom, alkyl, alkoxyl, aldehyde or hydroxylalkyl; each of $R_2$ and $R_4$ is independently selected from a hydrogen atom, hydroxyl, oxo, alkyl, alkoxyl; one or more hydrogen atoms of the alkyl, aldehyde, alkyl, alkoxyl can be independently substituted by hydroxyl, alkyl, or alkoxyl; provided that not all $R_1$, $R_2$, $R_3$ and $R_4$ are hydrogen atoms. Wherein, $R_1$ or $R_3$, $R_2$ or $R_4$, together with Y and Z, can form a saturated six-membered ring structure or a derivative structure thereof.

Preferably, the above alkyl group is preferably $C_1$-$C_4$ alkyl.

Preferably, at least one of the above $R_1$, $R_2$, $R_3$ and $R_4$ is a hydrogen atom.

Further preferably, the compound represented by Formula (I) is selected from one or more of the following structures:

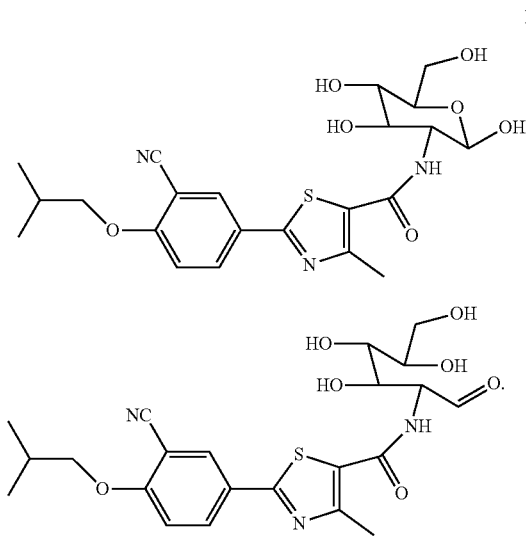

The compound of Formula (I) according to the present disclosure can exist in a form of stereoisomer, including all geometric, optical and conformational isomers, or mixtures thereof. The compound of Formula (I) according to the present disclosure can also contain one or more asymmetric carbon atoms, and thus can exhibit optical isomerism and/or diastereoisomerism. The present disclosure can use conventional techniques, such as chromatography or fractional crystallization, to separate enantiomers. The required optical isomers can also be obtained through the reaction of suitable and optically active starting materials under conditions which do not cause racemization or epimeric (stereoscopic) isomerization (i.e., the "chiral pool" method). The suitable starting materials are selected to react with a "chiral auxiliary", and enantiomer derivatives are separated by derivatization (i.e., resolution, including dynamic resolution) and conventional separation processes such as chromatography. Alternatively, the corresponding isomers can be obtained or separated after the reaction, through reacting with a suitable chiral reagent or chiral catalyst under conditions known to one skilled person in the art. All stereoisomers of the compound of Formula (I) and/or mixtures thereof are encompassed by the scope of the present disclosure.

The compound of the present disclosure can also exhibit tautomerism, and all tautomers and/or mixtures thereof are also encompassed by the scope of the present disclosure.

The pharmaceutically acceptable salt of the compound of Formula (I) according to the present disclosure includes common pharmaceutically acceptable salts formed by the compound of Formula (I) with an acid or base. The present disclosure has no particular limitation to the pharmaceutically acceptable salt. One skilled person in the art would understand, for example, the examples of a pharmaceutically acceptable acid addition salt include inorganic acid salts, in which the inorganic acid include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; organic acid salts, in which the organic acid include acids such as acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluene sulfonic acid, citric acid, tartaric acid and methanesulfonic acid; and salts of amino acids (e.g., arginine and the like), and salts of organic acids such as glucuronic acid. Examples of pharmaceutically acceptable base addition salts include inorganic base salt, in which preferred inorganic base is selected from sodium hydroxide, potassium hydroxide, calcium hydroxide, sodium carbonate, potassium bicarbonate, or the like.

The present disclosure also provides a method for preparing the compound represented by Formula (I) and/or a stereoisomer thereof. Particularly, the method comprises using 2-[3-cyano-4-isobutoxyphenyl]-4-methylthiazole-5-carboxylic acid as raw material, and adopting a compound containing

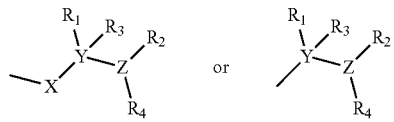

to perform a substitution reaction of carboxylhydroxyl, so as to obtain the compound. Wherein, the specific groups referred by X, Y, Z, $R_1$, $R_2$, $R_3$ and $R_4$ are as described above.

The compound represented by Formula (I) and/or stereoisomer thereof according to the present disclosure can also be obtained by other preparation methods. Based on the obtained compound represented by Formula (I) and/or stereoisomer thereof, the corresponding pharmaceutically acceptable salts can be obtained by using conventional salification methods in the art.

The present disclosure also provides use of the compound of Formula (I) or the salt or stereoisomer thereof in the preparation of a medicament for preventing or treating hyperuricemia and/or gout.

The present disclosure also provides a method for preventing or treating hyperuricemia and/or gout, which comprises administrating a compound of Formula (I) or a salt or stereoisomer thereof.

The compound of Formula (I) or a salt or stereoisomer thereof according to the present disclosure can be used to prepare dosage forms for various administration routes, wherein the compound of Formula (I) or a salt or stereoisomer thereof according to the present disclosure can be used for topical administration (e.g., to skin or to lung and/or respiratory tract) in a form of emulsion solution, suspension, aerosol or dry powder formulation; for systemic administration in a form of tablet, capsule, syrup, powders or granules, through for example oral administration; for parenteral administration in a form of solution or suspension; for subcutaneous administration; for rectal administration in a form of suppository; or, for transdermal administration.

The compound of Formula (I) or a pharmaceutically acceptable salt or stereoisomer thereof according to the present disclosure has better tolerance and safety, as well as excellent uric acid-lowering activity.

DETAILED DESCRIPTION

The following examples are used to illustrate the present disclosure, but not to limit the scope of the present disclosure.

The raw materials involved in the following examples are all commercially available. Hereinafter, raw material 2-[3- cyano-4-isobutoxyphenyl]-4-methylthiazole-5-carboxylic acid will be referred to as compound F.

Example 1: Preparation of F-1A

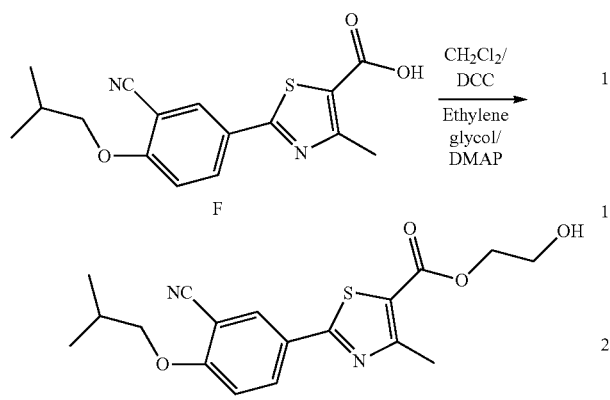

Weigh 1 g of compound F into a round bottom flask, add 100 mL of dichloromethane, and stir for 2 min to obtain an insoluble suspension. Then, add 386 mg of DMAP (4-dimethylaminopyridine), 1.3 g of DCC (dicyclohexylcarbodiimide), 3.5 mL of ethylene glycol successively. After reacting at room temperature for 24 hours, the resulted white solid was removed by filtration. The filtrate was washed with water and saturated brine, dried over anhydrous sodium sulfate and concentrated to obtain a crude product, which was purified by column chromatography to obtain 640 mg of solid, with yield of 56.1% and HPLC purity of 96.2%.

The structure of the resulted compound F-1A was characterized by the followings:

$^1$H-NMR (400 MHz, d$^6$DMSO): δ8.17 (s, 1H), 8.08-8.11 (d, 1H), 6.99-7.02 (d, 1H), 5.34 (s, 1H), 4.43-4.45 (t, 2H), 3.94-3.96 (d, 2H), 3.89-3.90 (t, 2H), 2.77 (s, 3H), 2.15-2.21 (m, 1H), 1.07-1.09 (d, 6H);

ESI-MS: 361.1 (M+1).

Example 2: Preparation of F-1B

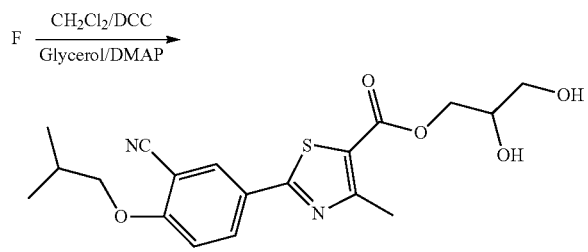

Weigh 1 g of compound F into a round bottom flask, add 100 mL of dichloromethane, stir for 2 min to obtain an insoluble suspension. Then, add 386 mg of DMAP (4-dimethylaminopyridine), 1.3 g of DCC (dicyclohexylcarbodiimide) and 5 mL of glycerol successively, react at room temperature, TLC monitor. After the reaction was completed, the resulted white solid was removed by filtration. The filtrate was washed with water and saturated brine, dried over anhydrous sodium sulfate and concentrated to obtain a crude product, purified by column chromatography to obtain 510 mg of solid, with yield of 43.0% and HPLC purity of 98.4%.

The structure of the resulted compound F-1B was characterized by the followings:

$^1$H-NMR (400 MHz, d$^6$DMSO): δ8.15 (s, 1H), 8.06-8.12 (d, 1H), 6.98-7.01 (d, 1H), 5.02 (s, 2H), 4.48-4.51 (m, 1H), 4.26-4.29 (m, 1H), 3.96-3.98 (d, 2H), 3.80-3.87 (m, 1H), 3.54-3.57 (m, 2H), 2.75 (s, 3H), 2.17-2.23 (m, 1H), 1.07-1.09 (d, 6H).

ESI-MS: 391.1 (M+1).

Example 3: Preparation of F-1C

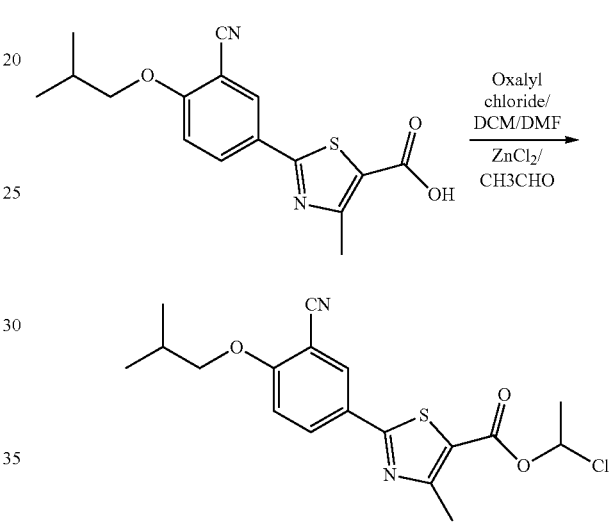

Weigh 20 g of compound F into a round bottom flask, add 200 mL of dichloromethane, 1 drop of DMF (N,N-dimethylformamide), stir for 2 min to obtain an insoluble suspension. Then, add 15.8 ml of oxalyl chloride dropwise in an ice bath, react at 25° C. After 4.5 hours, the reaction system was pale yellow, and the solvent was evaporated to obtain a pale yellow solid. Replace air in the reaction flask with nitrogen for 5 minutes, then add 300 mL of anhydrous dichloromethane. Replace air with nitrogen again, then add 15 ml of acetaldehyde and 32 ml of 1 mol/L zinc chloride solution dropwise in an ice bath. As the addition of zinc chloride, floccule began to appear in the system. After the completion of the addition, the reaction was continued for additional 5 hours at room temperature and then finished. The reaction system was washed repeatedly with 5% sodium bicarbonate solution, and a large amount of floccule appeared, and was filtered, washed with water and saturated brine, dried, concentrated, purified to obtain 21.1 g of colorless solid, with yield of 88.3% and HPLC purity of 98.5%.

The structure of the resulted compound F-1C was characterized by the followings:

$^1$H-NMR (400 MHz, d6DMSO): δ8.19 (s, 1H), 8.09-8.12 (dd, 1H), 7.0-7.03 (d, 1H), 6.69-6.74 (d, 1H), 3.89-3.90 (d, 2H), 2.78 (s, 3H), 2.17-2.25 (m, 1H), 1.90-1.91 (d, 3H), 1.07-1.09 (d, 6H).

ESI-MS: m/z 378.9, 380.9 (M+1).

Example 4: Preparation of Compound F-2A

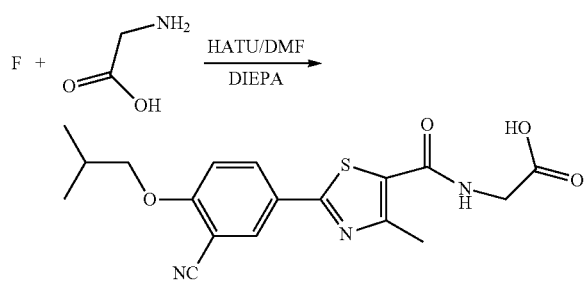

Weigh 3.16 g of compound F into a round bottom flask, add 25 mL of dimethylformamide, 0.75 g of glycine, 5.7 g of HATU [2-(7-azabenzotriazole)-N,N,N',N'-tetramethyluronium hexafluorophosphate] and 1 ml of DIPA (diisopropylaniline), stir the reaction at room temperature, TLC monitor the reaction. After the reaction was completed, reduce pressure and evaporate the solvent, then add 100 ml of ethyl acetate and 1 ml of glacial acetic acid to the system, shake repeatedly. Then, the system was washed with saturated brine, purified by column chromatography to obtain 2.29 g product, with yield of 61.3% and HPLC purity of 98.9%.

The structure of the resulted compound F-2A was characterized by the followings:

$^1$H-NMR (400 MHz, d$^6$DMSO): δ 12.78 (broad, 1H), 8.55-8.57 (d, 1H), 8.27 (s, 1H), 8.20-8.23 (d, 1H), 7.39-7.41 (d, 1H), 4.03-4.04 (d, 2H), 3.89-3.90 (d, 2H), 2.76 (s, 3H), 2.20-2.26 (m, 1H), 1.11-1.13 (d, 6H).

ESI-MS: m/z 372.1 (M-1).

Example 5: Preparation of Compound F-2B

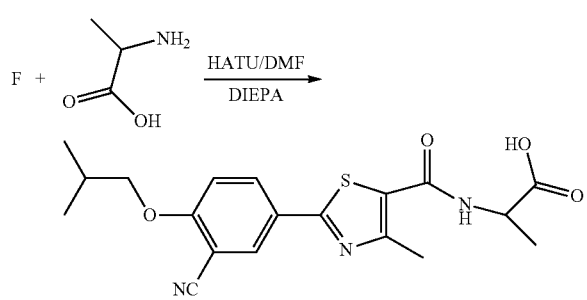

Weigh 3.16 g of compound F into a round bottom flask, add 25 mL of dimethylformamide, 0.89 g of glycine, 5.7 g HATU and 1.5 ml of DIPA, stir at room temperature, TLC monitor the reaction. After the reaction was completed, reduce pressure and evaporate the solvent, then add 100 ml of ethyl acetate and 1 ml of glacial acetic acid to the system, and shake repeatedly. Then, the system was washed with saturated brine, purified by column chromatography to obtain 2.21 g product, with yield of 57.1% and HPLC purity of 98.7%.

The structure of the resulted compound F-2B was characterized by the followings:

$^1$H-NMR (400 MHz, d$^6$DMSO): δ 12.71 (broad, 1H), 8.53-8.55 (d, 1H), 8.27 (s, 1H), 8.19-8.22 (d, 1H), 7.37-7.40 (d, 1H), 4.64-4.66 (m, 1H), 4.01-4.02 (d, 2H), 2.79 (s, 3H), 2.19-2.25 (m, 1H), 1.44 (d, 3H), 1.11-1.13 (d, 6H).

ESI-MS: m/z 386.1 (M-1).

Example 6: Preparation of Compound F-2C

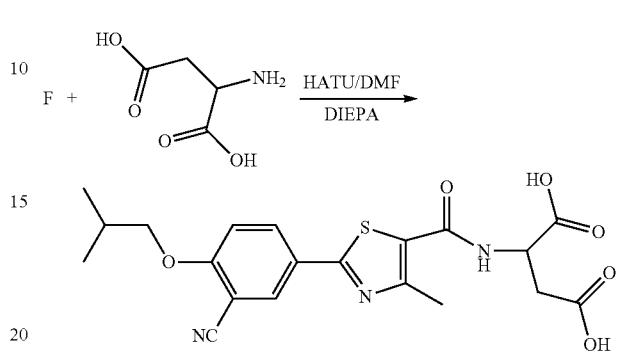

Weigh 3.16 g of compound F into a round bottom flask, add 25 mL of dimethylformamide, 1.33 g of aspartic acid, 5.7 g of HATU and 3 ml of DIPA, stir at room temperature, TLC monitor the reaction. After the reaction was completed, add 200 ml of ethyl acetate to the system, then add 4 ml of glacial acetic acid, and shake repeatedly. Then, the system was washed with saturated brine, purified by column chromatography to obtain 2.08 g, with yield of 48.2% and HPLC purity of 98.6%.

The structure of the resulted compound F-2C was characterized by the followings:

$^1$H-NMR (400 MHz, d$^6$DMSO): δ 12.74 (broad, 2H), 8.56-8.58 (d, 1H), 8.28 (s, 1H), 8.20-8.23 (d, 1H), 7.39-7.41 (d, 1H), 4.69-4.74 (m, 1H), 4.02-4.03 (d, 2H), 2.61-2.74 (m, 2H), 2.52 (s, 3H), 2.08-2.14 (m, 1H), 1.03-1.04 (d, 6H).

ESI-MS: m/z 430.1, 431.1 (M-1).

Example 7: Preparation of Compound F-2D

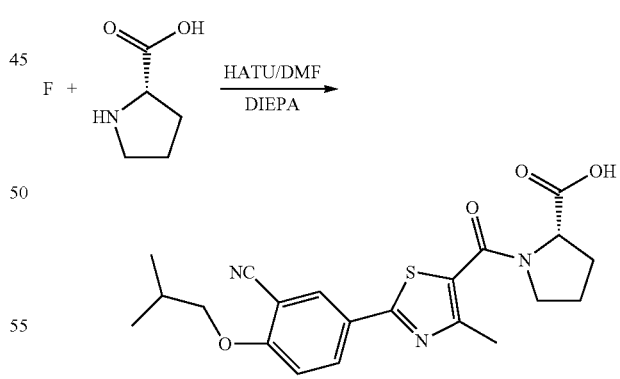

According to the above reactive equation, and referring to the method described in Example 6, 3.13 g of white powdery solid was obtained, with yield of 75.8% and HPLC purity of 97.6%.

The structure of the resulted compound F-2D was characterized by the followings:

$^1$H-NMR (400 MHz, d$^6$DMSO): δ 12.68 (broad, 1H), 8.28 (s, 1H), 8.20-8.23 (d, 1H), 7.39-7.41 (d, 1H), 4.67-4.71 (m, 1H), 4.0-4.01 (d, 2H), 2.71 (s, 3H), 2.01-2.08 (m, 1H), 1.87-1.90 (m, 1H), 1.67-1.70 (m, 1H), 1.63-1.66 (m, 2H), 1.43-1.46 (m, 2H), 1.0-1.01 (d, 6H).

ESI-MS: m/z 412.1 (M-1).

Example 8: Preparation of Compound F-3A

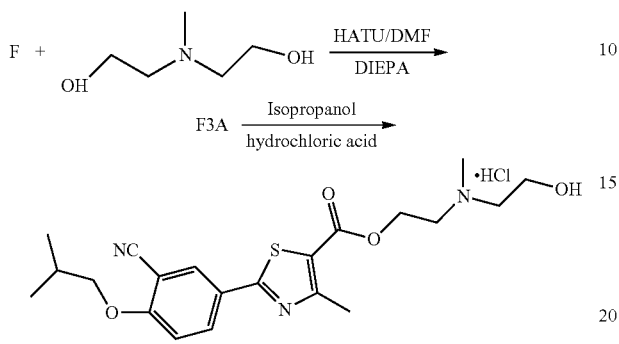

According to the above reactive equation and referring to the method described in Example 6, 2.84 g of white powdery solid F3A was obtained, with yield of 68.1%. Then, the white solid was dissolved in 15 ml of isopropanol under reflux, and then 1 ml of concentrated hydrochloric acid was added dropwise, stirred for 10 minutes, and stand overnight at room temperature to precipitate white solid. The resulted white solid was filtered, and washed with cold isopropanol to obtain 1.58 g product, with HPLC purity of 99.1%.

The structure of the resulted compound F-3A was characterized by the followings:

$^1$H-NMR (400 MHz, d$^6$DMSO): δ 10.26 (broad, 1H), 8.29-8.30 (d, 1H), 8.21-8.24 (s, 1H), 7.36-7.38 (m, 1H), 5.37 ((broad, 1H), 4.60 ((broad, 2H), 3.97-3.99 (d, 2H), 3.75-3.76 (d, 2H), 3.49-3.58 (broad, 2H), 3.20 (broad, 2H), 2.84 (s, 3H), 2.67 (s, 3H), 2.02-2.11 (m, 1H), 0.97-0.99 (s, 6H).

ESI-MS: m/z 418.2 (free base molecular weight M+1), 834.9 (2M+1).

Example 9: Preparation of Compound F-3B

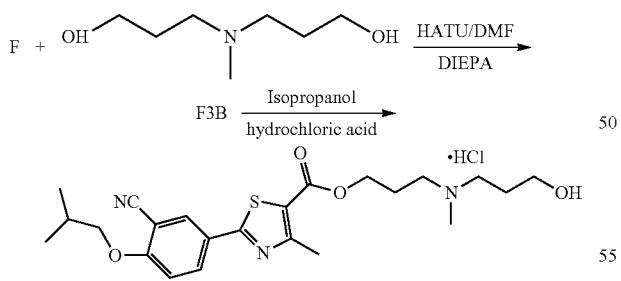

According to the above equation and referring to the method described in Example 6, 2.91 g of white powdery solid F3B was obtained, with yield of 65.2% and HPLC purity of 98.7%.

The structure of the resulted compound F-3B was characterized by the followings:

$^1$H-NMR (400 MHz, d$^6$DMSO): δ 10.19 (broad, 1H), 8.23-8.24 (d, 1H), 8.17-8.20 (s, 1H), 7.30-7.32 (m, 1H), 5.30 ((broad, 1H), 4.52 ((broad, 2H), 3.91-3.93 (d, 2H), 3.70-3.71 (d, 2H), 3.42-3.51 (broad, 2H), 3.15 (broad, 2H), 2.80 (s, 3H), 2.61 (s, 3H), 1.98-2.07 (m, 1H), 1.80-1.84 (m, 2H), 1.51-1.54 (m, 2H), 0.96-0.98 (s, 6H).

ESI-MS: m/z 446.2 (free base molecular weight +1).

Example 10: Preparation of Compounds F-4A, F-4B

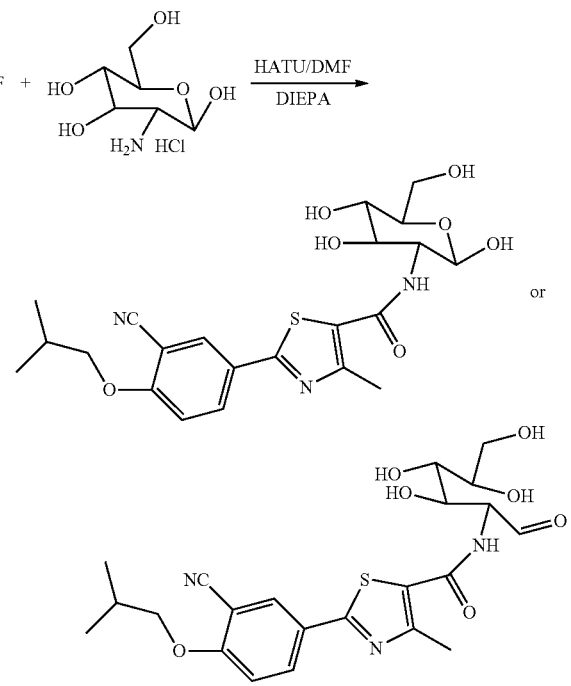

Weigh 3.16 g of compound F into a round bottom flask, add 15 mL of dimethylformamide and 15 ml of dimethylsulfoxide, 2.16 g of glucosamine hydrochloride, 5.7 g of HATU and 3 ml of DIPA, stir the reaction at room temperature for 24 hours, and then add 60 ml of ethyl ether to the system. The precipitated solid was purified by column chromatography to obtain 2.15 g product, with yield of 45.2% and HPLC purity of 98.1%.

The structure and characterization information of the resulted compound F-4A were as follows:

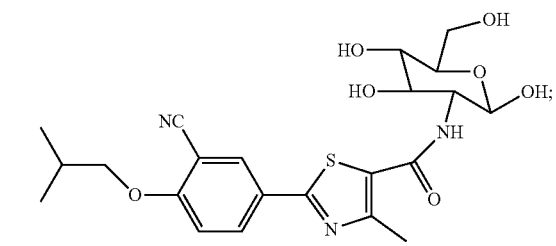 [SMILES: Cc1nc(-c2ccc(OCC(C)C)c(C#N)c2)sc1C(=O)NC1C(O)OC(CO)C(O)C1O]

$^1$H-NMR (400 MHz, d$^6$DMSO): δ8.26-8.28 (d, 1H), 8.20-8.23 (dd, 1H), 7.88-8.10 (m, 1H), 7.40-7.42 (d, 1H), 6.60-6.70 (m, 1H), 5.11-5.13 (t, 1H), 5.01-5.05 (m, 1H), 4.87-4.88 (d, 1H), 4.59-4.64 (m, 1H), 4.49-4.52 (t, 1H), 4.03-4.04 (d, 2H), 3.36-3.75 (m, 5H), 2.56 (s, 3H), 2.04-2.15 (m, 1H), 1.09-1.10 (d, 6H).

ESI-MS: m/z:478.1 (M+1).

The structure and characterization information of tautomer F-4B of compound F-4A were as follows:

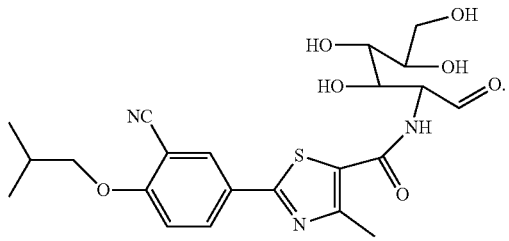 [SMILES: Cc1nc(-c2ccc(OCC(C)C)c(C#N)c2)sc1C(=O)NC(C=O)C(O)C(O)C(O)CO]

$^1$H-NMR (400 MHz, d$^6$DMSO+D$_2$O): δ8.17 (s, 1H), 8.11-8.13 (d, 1H), 7.27-7.29 (d, 1H), 5.11-5.13 (d, 0.67H), 4.63-4.65 (d, 034H), 3.94-3.95 (d, 2H), 3.23-3.84 (m, 6H), 2.53 (s, 3H), 2.03-2.06 (m, 1H), 0.97-0.98 (d, 6H).
ESI-MS: m/z:478.1 (M+1).

Example 11

In order to verify the tolerance and safety of the compounds of the present disclosure, this example provides an oral acute toxicity experiment, and uses existing drugs for treating gout or lowering uric acid for a comparative study.

1. Test Samples
Test samples: F-1A, F-1B, F-1C, F-2A, F-2B, F-2C, F-2D, F-3A, F-3B, F-4A prepared by the above examples 1-10, and febuxostat.
Formulation method: take each test sample and sodium carboxymethyl cellulose, grind to obtain 0.2% of sodium carboxymethyl cellulose suspension.

2. Test animals: ICR mice; body weight: 18-22 g.

3. Dose setting:
Preliminary experiments were firstly conducted. The mice were intragastric administrated with each test sample at a dose of 1600 mg/kg, and toxic reactions were observed. Preliminary experiments showed that compounds F-1A, F-1B, F-1C, F-2A, F-2B, F-2C, F-2D, F-3A, F-3B, F-4A had less toxicity, and no obvious toxicity symptom was observed in the mice at a dose of 1600 mg/kg, and no animal died. Preliminary experiments showed that febuxotan had a certain toxicity, and caused death in several mice at a dose of 1600 mg/kg.

On the basis of the preliminary experiments, the dose of each test sample for formal test was set, as shown in table 1.

TABLE 1

Dose set for each test sample in toxicity test

| Test sample | Dose (mg/kg) [Formulation concentration (mg/ml)] | Administration volume (ml/kg) | Remarks |
|---|---|---|---|
| Febuxostat | 800, 640, 512, 409.6, 327.7 [40.0, 32.0, 25.6, 20.48, 16.38] | 20 | Determining LD$_{50}$ or maximum administration dose (mg/kg) |
| F-1A | 3000[200*] | 25 | |
| F-1B | 3000[200*] | 25 | |
| F-1C | 3000[200*] | 25 | |
| F-2A | 3000[200*] | 25 | |
| F-2B | 3000[200*] | 25 | |
| F-2C | 3000[200*] | 25 | |
| F-2D | 3000[200*] | 25 | |

TABLE 1-continued

Dose set for each test sample in toxicity test

| Test sample | Dose (mg/kg) [Formulation concentration (mg/ml)] | Administration volume (ml/kg) | Remarks |
|---|---|---|---|
| F-3A | 3000[200*] | 25 | |
| F-3B | 3000[200*] | 25 | |
| F-4A | 3000[200*] | 25 | |

* Maximum formulation concentration.

4. Administration route: intragastric (ig) administration.

5. Experiment methods:
Laboratory environment: room temperature 24±2° C., relative humidity 60-70%.
Observation indexes: According to the above doses and the administration volumes, each test sample was formulated into a solution having the corresponding concentration through geometric proportion dilution, and was ig administrated once with the same volume. Various toxic symptoms and death of the mice were recorded, and dead animals were examined by autopsy.
Observation period: 14 days.

6. Test results
6.1 Abnormal reactions: Within 12 hours from ig administration of F-1A, F-1B, F-1C, F-2A, F-2B, F-2C, F-2D, F-3A, F-3B, F-4A and febuxostat, only several animals from the high-dose group of febuxostat showed reduced activity, and no abnormalities were observed in the other groups.

Within 24 hours from the administration, no animal deaths were observed in all dose groups of F-1A, F-1B, F-1C, F-2A, F-2B, F-2C, F-2D, F-3A, F-3B, F-4A, and several animals of the high-dose group of febuxotan died. At Day 8 after the administration, no death was observed for the survival animals of all the groups. The survival animals only showed reduced activity and emaciation, and no other obvious abnormalities were observed.

6.2 Autopsy results: The autopsy of dead animals of the high-dose group showed bilateral kidneys with pale color and urinary retention. No obvious abnormalities were observed in other organs. The autopsy of the survival animals showed that all the organs were normal. No obvious abnormalities were observed in the organs of all the survival animals of compounds F-1A, F-1B, F-1C, F-2A, F-2B, F-2C, F-2D, F-3A, F-3B, F-4A test groups.

6.3 Cause of death: After administration of febuxostat, the mice might die due to its toxicity to the urinary system, which eventually lead to systemic failure.

6.4 Table 2 shows the death and LD$_{50}$ values of ig administration of the test samples in mice.

TABLE 2

LD$_{50}$ values of ig administration of the test samples in mice (calculated by Bliss method)

| Compound | Dose (mg/kg) | Total number of animals | Number of dead animals | LD$_{50}$/ Maximum dose (mg/kg) |
|---|---|---|---|---|
| Febuxostat | 800 | 10 | 6 | 701.29 ± 47.6 |
| | 640 | 10 | 3 | |
| | 512 | 10 | 1 | |
| | 409.6 | 10 | 0 | |
| | 327.7 | 10 | 0 | |
| F-1A | 3000 | 10 | 0 | 3000 |
| F-1B | 3000 | 10 | 0 | 3000 |
| F-1C | 3000 | 10 | 0 | 3000 |

TABLE 2-continued

LD$_{50}$ values of ig administration of the test
samples in mice (calculated by Bliss method)

| Compound | Dose (mg/kg) | Total number of animals | Number of dead animals | LD$_{50}$/ Maximum dose (mg/kg) |
|---|---|---|---|---|
| F-2A | 3000 | 10 | 0 | 3000 |
| F-2B | 3000 | 10 | 0 | 3000 |
| F-2C | 3000 | 10 | 0 | 3000 |
| F-2D | 3000 | 10 | 0 | 3000 |
| F-3A | 3000 | 10 | 0 | 3000 |
| F-3B | 3000 | 10 | 0 | 3000 |
| F-4A | 3000 | 10 | 0 | 3000 |

Summary: Compounds F-1A, F-1B, F-1C, F-2A, F-2B, F-2C, F-2D, F-3A, F-3B, F-4A of the present disclosure are very well tolerated and safe, and the LD$_{50}$ values are 3000 mg/kg or more, and thus are significantly superior to the existing drugs.

Example 12

In order to verify the pharmacological activities of the compounds of the present disclosure, this example provides a pharmacodynamic screening experiment based on a rat model, in which exogenous uric acid is administered and uric acid decomposition is inhibited simultaneously, and positive drugs are selected as control.

1. Experimental animals: SD rats, free drinking and eating. Feed was sterilized by irradiation, and water was sterilized purified water. Adaptive feed for one week.

2. Experimental drugs: F-1A, F-1B, F-1C, F-2A, F-2B, F-2C, F-2D, F-3A, F-3B and F-4A, 1.0 g for each compound; febuxostat 1.0 g; febuxostat ethyl ester (ethyl 2-[3-cyano-4-isobutoxyphenyl]-4-methylthiazole-5-carboxylate) 1.0 g.

3. Drug formulation:

3.1 Formulation of compounds F-1A, F-1B, F-1C, F-2A, F-2B, F-2C, F-2D, F-3A, F-3B, F-4A: For each compound, take 100 mg of the compound, add 20 ml of 0.5% sodium carboxymethyl cellulose and grind, and then dilute to 100 ml.

3.2 Formulation of febuxostat and febuxostat ethyl ester: Take 140 mg of febuxostat or febuxostat ethyl ester, add 20 ml of 0.5% sodium carboxymethyl cellulose to grind, and then dilute to 100 ml respectively.

4. Experimental reagents, drugs and instruments:
Oteracil potassium (Oxonic acid), Uric acid (Uric), sodium carboxymethyl cellulose, Uric acid (UA) assay kit. US Multiskan MK3 Microplate Reader. Thermo Labsystems Multiskan Ascent V1 Plate Reader, Finland.

5. Grouping and administration

Except the blank group, the rest rats were modeled for 15 days, and then their serum uric acid levels were detected. The rats were equally divided into several groups according to the detected uric acid levels thereof.

Blank group: no drug administration, 10 animals

Model group: oral administration of 2 ml of 0.5% sodium carboxymethyl cellulose, QD, 10 animals.

Groups F-1A F-4A: each of 10 compounds was taken orally at 10 mg/kg, QD, and 10 animals per group.

Febuxostat group: oral administration of 14 mg/kg, QD, and 10 animals.

Febuxostat ethyl ester group: oral administration of 14 mg/kg, QD, and 10 animals.

6. Experimental methods and operation processes.

The blank group was not administered with any drug. Each of the rest groups was orally administrated with oteracil potassium 1.5 g/kg+uric acid 0.3 g/kg (dissolved in 0.5% sodium carboxymethyl cellulose), once a day on schedule, for 15 days. 0.5 ml of blood samples was drawn from orbit before the experiment and 13 days after the modelling, respectively, to separate serum and determine serum uric acid levels.

After successful modeling, the rats were equally divided into several groups according to the serum uric acid values thereof. After grouping, the rats were continued to be fed with the modeling drugs oteracil potassium 1.5 g/kg+uric acid 0.3 g/kg for additional two days. One hour after the last administration of the modelling drugs, the rats began to be intragastrically administrated with the test drugs. Three hours after the first administration, 0.5 ml of orbital venous blood was drawn from the orbit of the rats, centrifuged at 3000 RPM for 15 min, to obtain serum. The serum uric acid level of each rat was detected by using Uric acid (UA) assay kit, on Multiskan MK3 Microplate Reader (US), Thermo Labsystems Multiskan Ascent V1 Plate Reader (Finland).

7. Statistical processing and experimental results.

Data were expressed by mean±standard deviation ('x±SD), and analyzed by Excel 7.0 and SPPS 13.0 for Windows software. Q-test was used for the comparison between groups, and a self-paired t-test was used for the comparison of a group before and after administration. It indicated significant difference when P<0.05. The mainly obtained experiment results are shown in table 3.

TABLE 3

Effects of the compounds of the present disclosure on serum uric acid level of hyperuricemia rats

| Group | Administration dose (number of animals) (mg/kg) | Serum uric acid level (μmol/L) | | |
|---|---|---|---|---|
| | | Normal value | Value after 13 days of modeling | Value after 3 h of drug administration |
| Blank group | — (10) | 45.1 ± 4.0 | 50.6 ± 8.7 | 53.9 ± 12.8 |
| Model group | — (10) | 47.0 ± 7.5 | 157.9 ± 22.7 $^{c3}$ | 174.4 ± 39.9$^{c3}$ |
| Febuxostat | 14 (10) | 45.6 ± 7.6 | 153.1 ± 22.0$^{c3}$ | 86.6 ± 17.5$^{a3b3c3}$ |
| Febuxostat ethyl ester | 14 (10) | 46.5 ± 7.4 | 157.2 ± 22.9$^{c3}$ | 113.9 ± 24.9$^{a3b3c3}$ |
| F-1A | 10 (10) | 47.4 ± 6.6 | 156.1 ± 27.0$^{c3}$ | 71.0 ± 24.4$^{a3b3c1}$ |
| F-1B | 10 (10) | 44.1 ± 8.5 | 160.1 ± 25.8 $^{c3}$ | 67.5 ± 19.4$^{a3b3}$ |
| F-1C | 10 (10) | 44.6 ± 7.6 | 162.6 ± 33.2$^{c3}$ | 64.2 ± 28.1$^{a3b3}$ |
| F-2A | 10 (10) | 43.8 ± 8.4 | 163.0 ± 25.5$^{c3}$ | 78.3 ± 25.1$^{a3b3c2}$ |
| F-2B | 10 (10) | 46.3 ± 8.0 | 162.8 ± 44.0$^{c3}$ | 70.3 ± 16.4$^{a3b3c1}$ |
| F-2C | 10 (10) | 45.4 ± 6.7 | 158.9 ± 31.0$^{c3}$ | 68.6 ± 19.2$^{a3b3c1}$ |
| F-2D | 10 (10) | 46.5 ± 6.1 | 156.8 ± 24.5$^{c3}$ | 69.1 ± 23.4$^{a3b3c1}$ |

TABLE 3-continued

Effects of the compounds of the present disclosure on serum uric acid level of hyperuricemia rats

| Group | Administration dose (number of animals) (mg/kg) | Serum uric acid level (μmol/L) | | |
|---|---|---|---|---|
| | | Normal value | Value after 13 days of modeling | Value after 3 h of drug administration |
| F-3A | 10 (10) | 45.9 ± 5.7 | 160.4 ± 27.7$^{c3}$ | 64.1 ± 16.1$^{a3b3}$ |
| F-3B | 10 (10) | 44.2 ± 7.9 | 158.6 ± 21.6$^{c3}$ | 66.3 ± 17.1$^{a3b3}$ |
| F-4A | 10 (10) | 45.5 ± 7.3 | 160.8 ± 40.5$^{c3}$ | 71.4 ± 19.6$^{a3b3c1}$ |

Note:
Administration dose is in mg/kg. Compared with the model group, a3: $p < 0.001$. Compared with 13 days of modeling, in each group, b3: $p < 0.001$. Compared with the blank group, c1: $p < 0.05$, c2: $p < 0.01$, c3: $p < 0.001$.

It can be seen from the results shown in table 3 that, in this experiment, the rat hyperuricemia model, in which exogenous uric acid was administered and uric acid decomposition was inhibited simultaneously, was successfully established. The rats were intragastrically administered with a suspension of oteracil potassium 1.5 g/kg+uric acid 0.3 g/kg continuously for 15 days. There are significant differences in serum uric acid levels between the rats after and before the hyperuricemia modeling ($p<0.001$), indicating that the hyperuricemia model was successfully established.

Three hours after drug administration, the uric acid levels of the animals in each test drug group were significantly reduced as compared with those of the model group (a3, $p<0.001$), indicating that all the test drugs had uric acid-lowering effect. Nonetheless, there were still differences in specific effect of lowering uric acid among these groups. In particular, after the drug administration the uric acid levels of the animals administrated with compound F-1B, F-1C, F-3A or F-3B had no significant difference as compared with those of the blank group, and were very close to the normal value. Thus, compounds F-1B, F-1C, F-3A and F-3B have very obvious uric acid-lowering effects. The uric acid levels of the animals administrated with compounds F-1A, F-2B, F-2C, F-2D, F-4A were significantly different from those of the blank group (c1, $p<0.05$). The uric acid level of the group administrated with Compound F-2A was significantly different from the blank group (c2, $p<0.01$). It indicates that, though there was a certain difference between the uric acid level of the administrated animals with the normal value, its uric acid-lowering effect was still excellent. The positive control, febuxostat, had good effect on lowering uric acid. However, there was an extremely significant difference (c3,$p<0.001$) between the uric acid level of the group administrated with febuxostat and that of the blank group. It indicates that the uric acid levels of the animals administrated with febuxostat is quite different from the normal value, and the efficacy of febuxostat is inferior to the compounds of the present disclosure. Further, the efficacy of febuxostat ethyl ester, an intermediate of febuxostat, was inferior to febuxostat. This study indicates that the compounds of the present disclosure have excellent uric acid-lowering effect, which is better than the existing uric acid lowering drugs.

Example 13

In order to further study the pharmacological activity of the compounds of the present disclosure, as well as the relationship between the activity and the dose, this example selected several compounds of the present disclosure to conduct a dose-effect relationship study in a rat model, in which exogenous uric acid was administered and uric acid decomposition was inhibited simultaneously. A positive drug was used as a control.

1. Experimental animals: Male SPF grade SD rats weighing 110-150 grams. The animals were fed adaptively for 1 week, and were observed for body surface signs. The animals were free to drink and eat. All cages were sterilized at 121° C., feed was sterilized by irradiation, and water was sterilized purified water.

2. Experimental drugs: F-1C, F-2C, F-3A, 1.0 g for each compound; febuxostat (positive drug) 1.0 g; febuxostat ethyl ester (ethyl 2-[3-cyano-4-isobutoxyphenyl]-4-methylthiazole-5-carboxylate) 1.0 g;

3. Drug formulation:

3.1 Formulation of F-1C, F-2C, F-3A: Tor each of the compounds, take 100 mg, add 20 ml of 0.5% sodium carboxymethyl cellulose and grind, and then dilute to 100 ml.

3.2 Take 100 mg of febuxostat, add 20 ml of 0.5% sodium carboxymethyl cellulose and grind, and then dilute to 100 ml.

4. Reagents, drugs and instruments for testing:

Oteracil potassium (Oxonic acid), Uric acid (Uric), sodium carboxymethyl cellulose, Uric acid (UA) assay kit. Automatic Bio-Chemistry Analyzer: AU480 automatic Bio-Chemistry Analyzer, Olympus corporation, Japan.

5. Grouping and administration:

Except the blank group, the rest rats were modeled for 15 days and then their serum uric acid levels were detected. The rats were equally divided into several groups according to the detected uric acid levels thereof.

Blank group: no drug administration, 10 animals.

Model group: oral administration of 2 ml of 0.5% sodium carboxymethyl cellulose, QD, 10 animals.

F-1C, F-2C and F-3A groups: each compound was taken orally at 3 doses, i.e., 2.5, 5 and 10 mg/kg; QD; and 10 animals for each dose group.

Febuxostat group: oral administration of 10 mg/kg, QD, and 10 animals.

Febuxostat ethyl ester group: oral administration of 10 mg/kg, QD, and 10 animals.

6. Experimental methods and operation processes:

The blank group was not administrated with any drug. Each of the rest groups was orally administrated with oteracil potassium 1 g/kg and uric acid 0.3 g/kg and intraperitoneally injected with 0.1 g/kg uric acid (dissolved in 0.5% sodium carboxymethyl cellulose), once a day on schedule, for 15 days. 0.5 ml of blood samples was drawn from orbit before the experiment and 13 days after the modelling, respectively, to separated serum for determining serum uric acid levels.

After successful modeling, the rats were equally divided into several groups according to the serum uric acid values thereof, and then were intragastrically administrated with the test drugs. Three hours after the first administration, 0.5 ml of orbital venous blood was drawn from the orbit of the rats, centrifuged at 3000 RPM for 15 min, to obtain for determining the serum uric acid level of each rat.

7. Statistical processing and experimental results:

Data were expressed by mean±standard deviation ('x±SD), and analyzed by Excel 7.0 and SPPS 13.0 for Windows software. Q-test was used for the comparison between groups, and the self-paired t-test was used for the comparison of a group before and after administration. It indicated significant difference when P<0.05. The mainly obtained experiment results are shown in table 4.

TABLE 4

Effects of different doses of the compounds of the present disclosure on serum uric acid level in hyperuricemia rats

| Group | Administration dose (number of animals) (mg/kg) | Serum uric acid content (μmol/L) | | |
|---|---|---|---|---|
| | | Normal value | Value after 13 days of modeling | Value after 3 h of drug administration |
| Blank group | — (10) | 30.2 ± 2.9 | 35.5 ± 4.0 | 37.4 ± 5.1 |
| Model group | — (10) | 30.5 ± 2.7 | 159.5 ± 22.4$^{a3}$ | 226.2 ± 35.2$^{a3}$ |
| Febuxostat | 10 (10) | 31.7 ± 1.9 | 159.1 ± 30.9$^{a3}$ | 140.8 ± 33.5$^{a3,\ b3}$ |
| Febuxostat ethyl ester | 10 (10) | 30.9 ± 1.5 | 163.2 ± 29.8$^{a3}$ | 177.3 ± 38.6$^{a3}$ |
| F-1C | 10 (10) | 32.1 ± 3.0 | 161.0 ± 21.5$^{a3}$ | 100.1 ± 25.8$^{a3,\ b3,\ c3}$ |
| | 5 (10) | 31.9 ± 2.7 | 161.2 ± 27.6$^{a3}$ | 146.9 ± 19.5$^{a3,\ b3}$ |
| | 2.5 (10) | 31.5 ± 3.3 | 160.5 ± 34.9$^{a3}$ | 189.8 ± 25.3$^{a3}$ |
| F-2C | 10 (10) | 32.3 ± 1.5 | 160.0 ± 29.3$^{a3}$ | 107.3 ± 21.2$^{a3,\ b3,\ c3}$ |
| | 5 (10) | 29.6 ± 2.5 | 159.7 ± 23.4$^{a3}$ | 131.9 ± 29.7$^{a3,\ b3}$ |
| | 2.5 (10) | 31.6 ± 2.6 | 161.3 ± 26.8$^{a3}$ | 172.7 ± 33.9$^{a3}$ |
| F-3A | 10 (10) | 33.0 ± 4.1 | 161.5 ± 34.1$^{a3}$ | 82.3 ± 16.8$^{a3,\ b3,\ c3}$ |
| | 5 (10) | 30.8 ± 3.2 | 159.5 ± 25.6$^{a3}$ | 137.6 ± 24.3$^{a3,\ b3}$ |
| | 2.5 (10) | 30.6 ± 2.9 | 159.1 ± 21.0$^{a3}$ | 173.4 ± 32.7$^{a3,\ b3}$ |

Note:
Compared with the blank group, a3: p < 0.001; Compared with the model group, b3: p < 0.001; Compared with the febuxostat group, c3: p < 0.001.

It can be seen from the results shown in table 4 that after the rats were continuously intragastrically administrated with oteracil potassium 1 g/kg+uric acid 0.3 g/kg suspension, and intraperitoneally injected with 0.1 g/kg uric acid (dissolved in 0.5% sodium carboxymethyl cellulose) for 15 days, there are significant differences (p<0.001) in serum uric acid levels between the rats after and before the hyperuricemia modeling. In this experiment, the rat uricemia model, in which exogenous uric acid was administered and uric acid decomposition was inhibited simultaneously, was successfully established.

Three hours after the administration of the test drugs, the uric acid level of each test drug group was lower than that of the model group, indicating that each test drug had a certain effect on lowering uric acid. With comparing each dose group, the compounds of the present disclosure showed a good dose-dependent effect, the higher the dose, the better the effect of lowering uric acid will be. In addition, the uric acid-lowering effect of the compounds of the present disclosure, at the same dose, is obviously better than that of the positive drug (p<0.001).

The above examples are only for illustrating the preferred embodiments of the present disclosure, and are not intended to limit the scope of the present disclosure. Without departing from the spirit of the present disclosure, various modifications and improvements can be made by those skilled in the art to the technical solutions of the present disclosure, and all shall fall within the scope of protection defined by the claims of the present disclosure.

The invention claimed is:

1. A thiazole-5-carboxylic acid derivative represented by Formula (I):

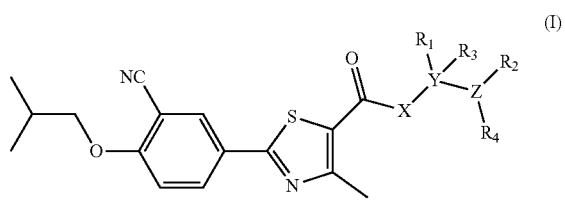

wherein:

X is selected from oxygen or nitrogen; both Y and Z are carbon;

each of $R_1$, $R_2$, $R_3$, $R_4$ is independently selected from a hydrogen atom, halogen, oxo, and substituted or unsubstituted amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl;

wherein substituted is defined as each of one or more hydrogen atoms of the above amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl is independently substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, alkyl, hydroxyalkyl, carboxyalkyl, aminoalkyl or alkylaminoalkyl;

provided that not all $R_1$, $R_2$, $R_3$ and $R_4$ are hydrogen atoms; and when each of $R_1$, $R_2$, $R_3$, and $R_4$ is selected from a group consisting of hydrogen atom and alkyl only, at least one hydrogen atom of the alkyl is substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, hydroxyalkyl, carboxyalkyl, aminoalkyl or alkylaminoalkyl, or X is nitrogen: 1) the Y and Z, together with R₁ or R₃, and R₂ or R₄, form a pyranose ring or a derivative structure thereof; or 2) the X, Y, and Z, together with R₂ or R₄, form a saturated pyrrole ring or a derivative structure thereof, and, a stereoisomer and/or pharmaceutically acceptable salt thereof.

2. The thiazole-5-carboxylic acid derivative according to claim 1, wherein each of the $R_1$, $R_2$, $R_3$ and $R_4$ is independently selected from a hydrogen atom, halogen, hydroxyl, oxo, aldehyde, carboxyl, amino, alkyl, halogenated alkyl, aminoalkyl, aminoalkylamino, alkoxyl, alkyloxyalkyl, alkyloxyalkyloxy, alkylcarbonyl, alkylcarbonyloxy, alkyloxycarbonyl, alkylamino, alkylaminoalkyl, hydroxylalkylamino, hydroxylalkylaminoalkyl, alkylaminoalkyloxycarbonyl, hydroxylalkyl, hydroxylalkyloxy, carboxylalkyl or aminoalkyl.

3. The thiazole-5-carboxylic acid derivative according to claim 2, wherein the alkyl is $C_1$-$C_4$ alkyl.

4. The thiazole-5-carboxylic acid derivative according to claim 1, wherein the compound represented by Formula (I) is selected from one or more of the following structures:

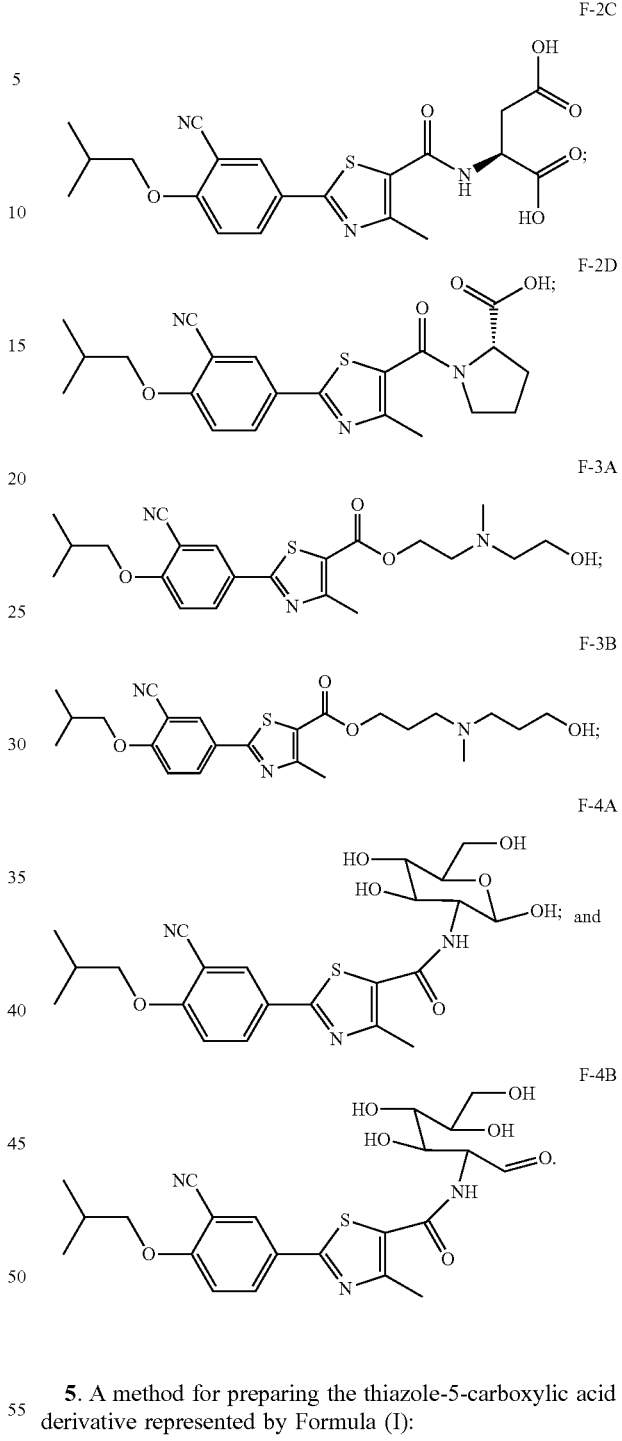

5. A method for preparing the thiazole-5-carboxylic acid derivative represented by Formula (I):

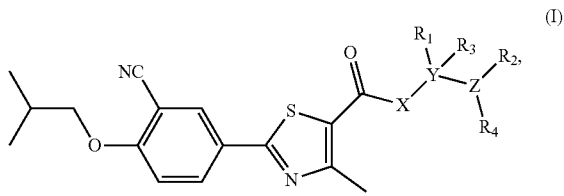

comprising using 2-[3-cyano-4-isobutoxyphenyl]-4-methylthiazole-5-carboxylic acid as a raw material, and adopting a compound containing a group

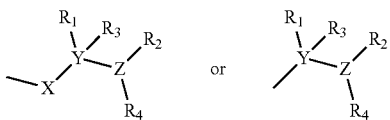

to perform a substitution reaction of carboxylhydroxyl, so as to obtain the thiazole-5-carboxylic acid derivative;
wherein,
X is selected from oxygen or nitrogen; both Y and Z are carbon;
each of $R_1$, $R_2$, $R_3$, $R_4$ is independently selected from a hydrogen atom, halogen, oxo, and substituted or unsubstituted amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl;
wherein substituted is defined as each of one or more hydrogen atoms of the above amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl is independently substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, alkyl, hydroxyalkyl, carboxyalkyl, aminoalkyl or alkylaminoalkyl;
provided that not all $R_1$, $R_2$, $R_3$ and $R_4$ are hydrogen atoms; and when each of $R_1$, $R_2$, $R_3$, and $R_4$ is selected from a group consisting of hydrogen atom and alkyl only, at least one hydrogen atom of the alkyl is substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, hydroxyalkyl, carboxyalkyl, aminoalkyl or alkylaminoalkyl;
or
X is nitrogen: 1) the Y and Z, together with $R_1$ or $R_3$, and $R_2$ or $R_4$, form a pyranose ring or a derivative structure thereof; or 2) the X, Y, and Z, together with $R_2$ or $R_4$, form a saturate d pyrrole ring or a derivative structure thereof.

6. A method for treating hyperuricemia and/or gout, comprising administrating a therapeutically effective amount of the thiazole-5-carboxylic acid derivative represented by Formula (I):

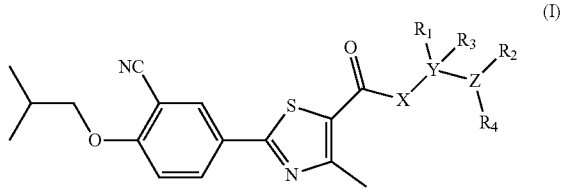

(I)

wherein:
X is selected from oxygen or nitrogen; both Y and Z are carbon;
each of $R_1$, $R_2$, $R_3$, $R_4$ is independently selected from a hydrogen atom, halogen, oxo, and substituted or unsubstituted amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl;
wherein substituted is defined as each of one or more hydrogen atoms of the above amino, alkylamino, aldehyde, alkyl, aminoalkyl, hydroxylalkyl, hydroxyl, alkoxyl, alkylcarbonyloxy, carboxyl, alkylcarbonyl or alkyloxycarbonyl is independently substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, alkyl, hydroxyalkyl, carboxyalkyl, aminoalkyl or alkylaminoalkyl;
provided that not all $R_1$, $R_2$, $R_3$ and $R_4$ are hydrogen atoms; and when each of $R_1$, $R_2$, $R_3$, and $R_4$ is selected from a group consisting of hydrogen atom and alkyl only, at least one hydrogen atom of the alkyl is substituted by halogen, hydroxyl, alkoxyl, alkylcarbonyloxy, aldehyde, carboxyl, alkylcarbonyl, alkyloxycarbonyl, alkylaminoalkyloxycarbonyl, amino, alkylamino, hydroxyalkyl, carboxyalkyl, aminoalkyl or alkylaminoalkyl;
or
X is nitrogen: 1) the Y and Z, together with $R_1$ or $R_3$, and $R_2$ or $R_4$, form a pyranose ring or a derivative structure thereof; or 2) the X, Y, and Z, together with $R_2$ or $R_4$, form a saturate d pyrrole ring or a derivative structure thereof,
and a stereoisomer and/or pharmaceutically acceptable salt thereof, to a subject in need thereof.

7. The method according to claim 6, wherein each of the $R_1$, $R_2$, $R_3$ and $R_4$ is independently selected from a hydrogen atom, halogen, hydroxyl, oxo, aldehyde, carboxyl, amino, alkyl, halogenated alkyl, aminoalkyl, aminoalkylamino, alkoxyl, alkyloxyalkyl, alkyloxyalkyloxy, alkylcarbonyl, alkylcarbonyloxy, alkyloxycarbonyl, alkylamino, alkylamino alkyl, hydroxylalkylamino, hydroxylalkylamino alkyl, alkylaminoalkyloxycarbonyl, hydroxylalkyl, hydroxylalkyloxy, carboxylalkyl or aminoalkyl.

8. The method according to claim 7, wherein the alkyl is $C_1$-$C_4$ alkyl.

9. The method according to claim 6, wherein the compound represented by Formula (I) is selected from one or more of the following structures:

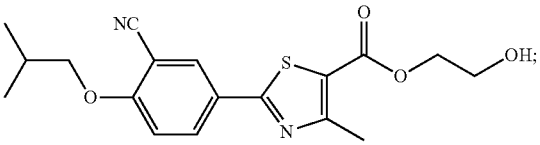

F-1A

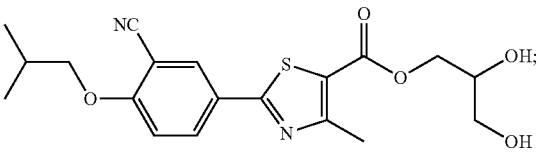

F-1B

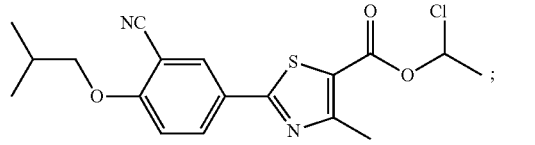

F-1C

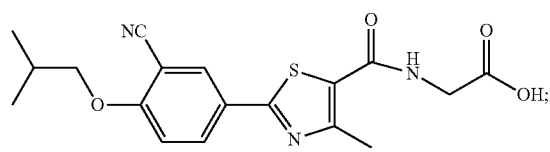
F-2A
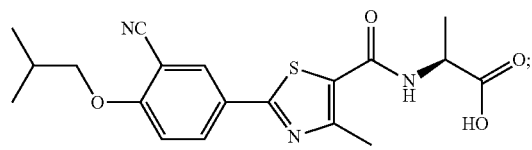
F-2B
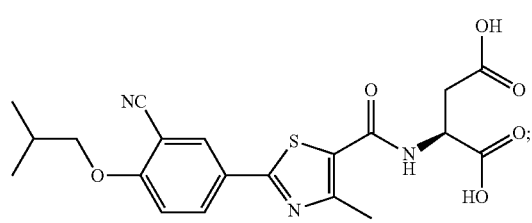
F-2C
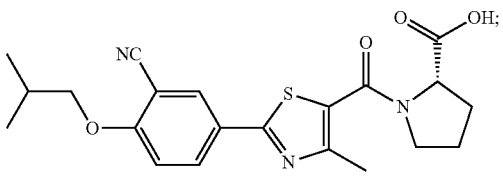
F-2D
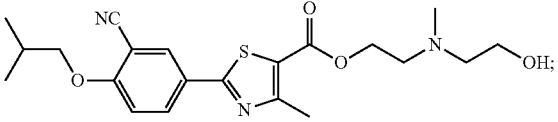
F-3A
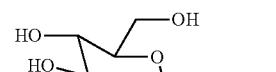
F-3B
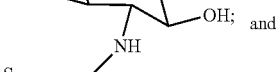
F-4A
and
F-4B
* * * * *